(12) United States Patent  
Gu

(10) Patent No.: US 8,679,308 B2  
(45) Date of Patent: Mar. 25, 2014

(54) BIOSENSOR MEMBRANE AND METHODS RELATED THERETO

(75) Inventor: Yuandong Gu, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 1102 days.

(21) Appl. No.: 11/375,910

(22) Filed: Mar. 15, 2006

(65) Prior Publication Data

US 2007/0215465 A1 Sep. 20, 2007

(51) Int. Cl.  
*G01N 27/327* (2006.01)

(52) U.S. Cl.  
USPC .......... 204/403.01; 205/777.5; 205/778; 204/403.05; 204/403.06

(58) Field of Classification Search  
USPC .......... 204/400, 403–403.06, 403.14, 418, 204/419; 205/777, 777.5, 792, 778  
See application file for complete search history.

(56) References Cited

U.S. PATENT DOCUMENTS

| | | | |
|---|---|---|---|
| 4,562,157 A | 12/1985 | Lowe et al. | |
| 4,909,921 A | 3/1990 | Ito | |
| 5,118,404 A * | 6/1992 | Saito | 205/778 |
| 5,309,085 A | 5/1994 | Sohn | |
| 5,543,024 A | 8/1996 | Hanazato et al. | |
| 6,464,848 B1 * | 10/2002 | Matsumoto | 204/403.06 |
| 6,746,582 B2 * | 6/2004 | Heller et al. | 204/403.06 |
| 2003/0134100 A1 * | 7/2003 | Mao et al. | 428/304.4 |
| 2004/0256685 A1 | 12/2004 | Chou et al. | |

FOREIGN PATENT DOCUMENTS

| | | |
|---|---|---|
| DE | 102004003793 | 11/2005 |
| DE | 19909841 | 9/2007 |
| WO | WO-02085500 | 10/2002 |

OTHER PUBLICATIONS

Hua et al. Cell Biochemistry and Biophysics, 2003, 23-43.*  
Ram et al., Biosensor & Bioelectronics, 2001, 16, 849-856.*  
Katrlik et al. Acta Facult . Pharm. Univ, Comenianae, 52, 2005, 116-124.*  
DrugBank data sheet on polystyrene sulfonate.*  
Ferreyra et al., Electrochimica Acta, 49, 2004 477-484.*  
Dzyadevych, S. V., et al., "Biosensors based on enzyme field-effect transistors for determination of some substrates and inhibitors", *Anal Bioanal Chem*, 377, (2003),496Å?506.  
Constatine, C. A., et al., "Layer-by-layer self-assembled chitosan/poly(thiophene-3-acetic acid) and organophosphorus hydrolase multilayers", *Journal American Chemical Society*, 125, (2003),1805-1809.  
Nguyen, Q. T., et al., "Simple Method for Immobilization of biomacromolecules onto membranes of different types", *Journal of membrane Science, Elsevier Scientific Publ. Company*, 213 (1-2), (Mar. 2003),85-95.

(Continued)

*Primary Examiner* — Luan Van  
*Assistant Examiner* — Gurpreet Kaur  
(74) *Attorney, Agent, or Firm* — Schwegman, Lundberg & Woessner, P.A.

(57) ABSTRACT

Embodiments of the present invention relate to a sensor membrane. The sensor membrane comprises one or more conversion layers wherein the one or more conversion layers are capable of converting a non-charged analyte into a charged species, one or more polymeric layers wherein the one or more polymeric layers act as matrices to host the one or more conversion layers and wherein the one or more conversion layers and one or more polymeric layers create oppositely charged regions within the membrane.

15 Claims, 2 Drawing Sheets

(56) References Cited

OTHER PUBLICATIONS

Smuleac, V., et al., "Layer-by-layer-assembled microfiltration membranes for biomolecule immobilization and enzymatic catalysis", *Langmuir*, 22, (Oct. 2006), 10118-10124.

Yu, A., et al., "Enzyme Multilayer-Modified Porous Membranes as Biocatalysts", *Chemistry of Materials, American Chemical Society*, 17(1), (2005), 171-175.

\* cited by examiner

BIOSENSOR MEMBRANE AND METHODS RELATED THERETO

FIELD OF THE INVENTION

Embodiments of the present invention relate to layered membranes for use with biosensors. More specifically, the embodiments of the present invention relate to alternately charged layers within a membrane for use with biosensors such as ion selective field effect transistor (ISFET)-based and enzyme field effect transistor (EnFET)-based biosensors in aqueous environments.

BACKGROUND

Biosensors, which refer to sensors utilizing a biological or biologically derived component in a transduction process, are frequently used as analytical tools in fields such as medicine, drinking water and food control. Biosensors can provide sensitive, fast, repetitive and cheap measurements for the detection, quantification and monitoring of different biological and chemical compounds.

One class of biosensor, called an ion selective field effect transistor (ISFET), is based on field effect transistor (FET) technology used in electronics, such as an enhanced mode metal oxide semiconductor field effect transistor (MOSFET). In an ISFET, a variation in the concentration of the ions of interest provides the variable gate voltage to control the conductivity of the channel. One specific type of ISFET is an enzyme field effect transistor (EnFET), which utilizes an immobilized enzyme to create a detectable species. Other types of biosensors include pH-based or ion selective electrodes. The ion or target species detected can be monitored or measured by using electrochemical, optical, calorimetric or acoustical means, for example.

A specific challenge for the use of biosensors, and specifically ISFETs and pH-based electrodes, in biological fluids, is the response of the sensor in a highly buffered environment. For example, blood plasma may contain about 40 mM of carbonate buffer. The high buffer concentration diminishes the ionic change of the analyte species that the sensor detects, therefore decreasing its sensitivity. In other situations, a conversion may occur at too high a rate for accurate detection and an increased buffer concentration would extend the dynamic range of the sensor for the target analyte or species.

SUMMARY

Embodiments of the present invention relate to a sensor membrane. The sensor membrane comprises one or more conversion layers wherein the one or more conversion layers are capable of converting a non-charged analyte into a charged species, one or more polymeric layers wherein the one or more polymeric layers act as matrices to host the one or more conversion layers and wherein the one or more conversion layers and one or more polymeric layers create oppositely charged regions within the membrane.

In addition, embodiments of the present invention relate to a sensor. Embodiments of the present invention also relate to methods of detecting an analyte with a sensor utilizing a layered membrane. Further, embodiments of the present invention relate to making a layered membrane on a sensor surface.

DETAILED DESCRIPTION

References in the specification to "one embodiment," "an embodiment," "an example embodiment," indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Embodiments of the present invention provide a layered membrane for utilization with a biosensor and methods thereto. The layered membrane comprises polyelectrolyte or polymeric layers and conversion layers that are formed to control the inclusion or exclusion of buffering species from an aqueous environment into the layered membrane. By controlling the buffering environment within the layered membrane, a sensor can detect an analyte or detectable species in an optimum state for accurate measurement. The buffering environment of the layered membrane can be optimized by customizing the layering of the membrane to the aqueous environment and to the specific analyte to be detected.

Figure 1:
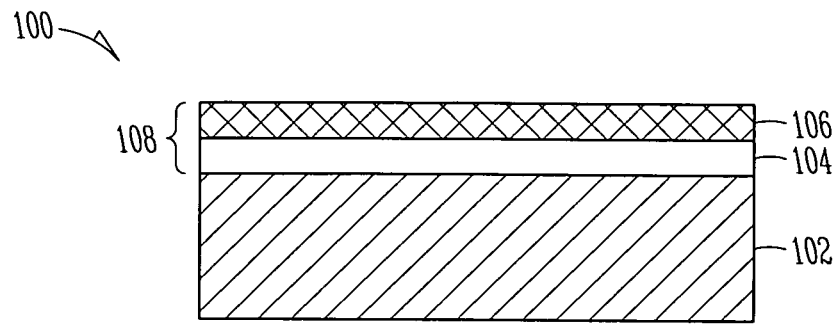
FIG. 1 illustrates a cross-sectional view of a sensor surface and layered membrane, according to some embodiments of the invention.

Referring to FIG. 1, a cross-sectional view of a sensor surface and layered membrane is shown, according to some embodiments of the invention. A sensor 100 comprises a sensor surface 102. A layered membrane 108 contacts the sensor surface 102 and comprises charged layers 104 and 106.

The sensor 100 can be any sensor capable of detecting an analyte within an aqueous environment. A biosensor is one type of sensor that can utilize the layered membrane embodiments. A biosensor may be defined as a sensor comprising a bioselective membrane in direct contact with a physical transducer, which transforms a biorecognition event into a signal, such as an electrical or optical signal. Biosensors also refer to sensors that determine the concentration of substances and other parameters of biological interest even where the sensor does not utilize a biological system directly. Examples of a biological system used by a biosensor are enzymatic conversions, whole cell metabolism, ligand binding and antibody-antigen reaction. Examples of biosensors may be an ion selective field effect transistor (ISFET) or an enzyme field effect transistor (EnFET). A sensor, such as a biosensor, typically comprises a conversion species that converts a substrate into a product or an analyte into a converted analyte. In the case of a transistor-based sensor, such as an ISFET or EnFET, the layered membrane of the embodiments of the present invention may act as part of the gate structure that controls the current to the transistor. A transducer may be used to convert the reaction to a signal, such as an electrical signal. The transducer may act as a detector or a detector may be used in place of the transducer. The output may optionally be amplified, processed and displayed.

The layered membrane 108 comprises polyelectrolyte or polymeric layers and conversion layers, which may be oppositely charged layers 104 and 106. A polyelectrolyte is a polymer whose repeating units bear an electrolyte group. The electrolyte groups dissociate in aqueous solutions, making the polymers charged. Examples of polyelectrolytes are poly (sodium styrene sulfonate) (PSS) and poly(acrylic acid) (PAA). A conversion layer may comprise a conversion species. A conversion species is capable of converting an analyte to a detectable species. A conversion species may be an enzyme or oxidizing agent, for example. The conversion layer may be a separate layer from the polyelectrolyte layers or may be part of a polyelectrolyte layer. One or more of the polyelectrolyte layers may also be a conversion layer or comprise a conversion species. The alternating layers within the layered membrane may be oppositely charged or create oppositely charged regions within the membrane. For example, a positive conversion layer may be placed next to a positive polymeric layer (creating a positive region), which is then placed next to a negative polymeric layer.

One or more polyelectrolyte layers that alternate within the layered membrane 108 are purposely selected to create an optimal buffering environment within the layered membrane 108. An example of a buffering species found in blood, carbonate ion, can be excluded by utilizing a negatively charged polyelectrolyte membrane, such as a polyacrylic acid with a pKa around 4.5. Some glucose sensors detect the hydrogen ions produced by a reaction with glucose oxidase and operate within the pH range of about 5 to about 7.4. A strong negatively charged polyelectrolyte, such as poly(sodium sulfonate) with a pKa of about 2, would decrease the buffering species movement into the layered membrane 108 and therefore increase the sensitivity of the sensor response. In another example, hydroxide ions are produced by the reaction utilized by urease in a urea sensor and the operating pH is around 7.4 to about 9. Polyacrylic acid could then be chosen to provide an optimum buffering environment. For creatinine sensors, current sensors tend to be overly sensitive and an increase in the buffering species within the layered membrane 108 would be desirable. By using a positively charged polyelectrolyte, such as polylysine, the layered membrane 108 would attract more buffering species, such as carbonate, into the membrane and decrease the sensor response. The combination of polyelectrolyte layers and conversion layers can be specifically chosen to provide an optimum detection environment for the target analyte. Polyelectrolytes may be chosen such that their pKa values are below the physiological condition and the operating pH of the sensor. The polyelectrolytes pKa value may be two pH units or more below the physiological condition and operating pH of the sensor, for example.

Figure 2:
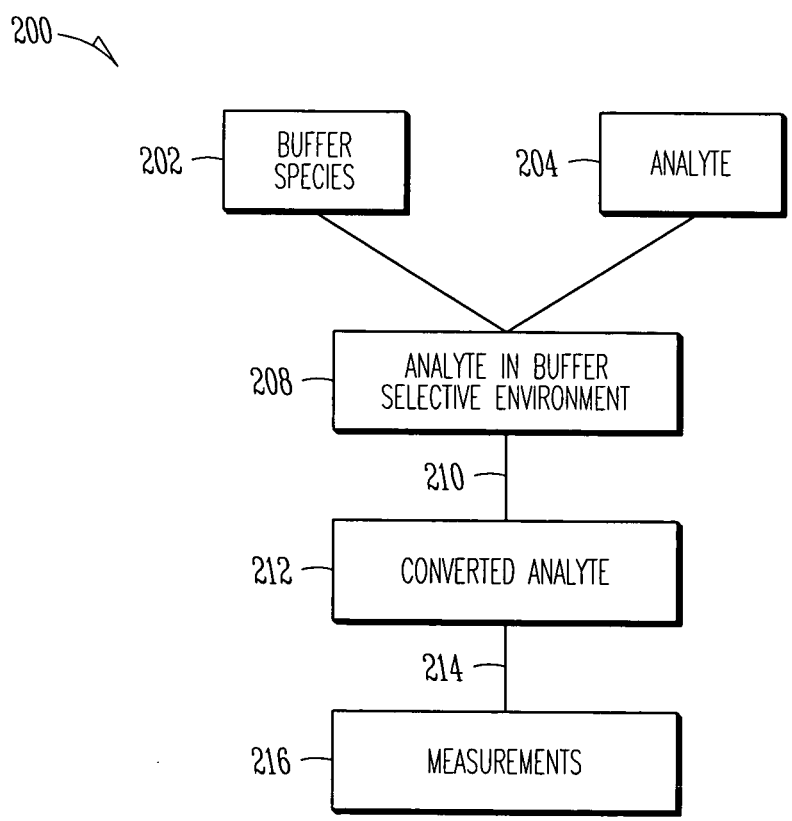
FIG. 2 illustrates a block flow diagram of a method to detect an analyte with a sensor utilizing a layered membrane, according to some embodiments of the invention.

Referring to FIG. 2, a block flow diagram of a method 200 to detect an analyte with a sensor utilizing a layered membrane is shown, according to some embodiments of the invention. An analyte 204 and buffer species 202 contact 206 a layered membrane in solution to provide an analyte in a buffer selective environment 208. The layered membrane converts 210 the analyte in the buffer selected environment 208 to a detectable species, referred to as a converted analyte 212. The converted analyte 212 is then detected 214 which produces measurements 216, such as concentration measurements of the converted analyte 212.

The converted analyte 212 may be detected 214 by utilizing the heat output (calorimetric detection), changes in the distribution of charges causing an electrical potential (potentiometric detection), movement of electrons produced in an oxidation-reduction reaction (amperometric detection), light output during the reaction or a light absorbance difference between analyte and converted analyte (optical detection) and the effects due to the mass of the analyte or converted analyte (piezo-electric detection), as examples.

Figure 3:
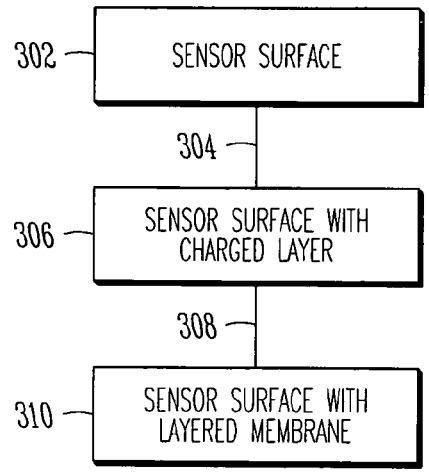
FIG. 3 illustrates a block flow diagram of a method of making a layered membrane on a sensor surface, according to some embodiments of the invention.

Referring to FIG. 3, a block flow diagram of a method 300 of making a layered membrane on a sensor surface is shown, according to some embodiments of the invention. A sensor surface 302 is contacted 304 with a charged layer to create a sensor surface with charged layer 306. Contacting may refer to dipping, for example. The charged layer 306 may be a positively charged or negatively charged polyelectrolyte solution. An example of a positively charged polyelectrolyte solution is a polycyclic aromatic hydrocarbon (PAH). An example of a negatively charged polyelectrolyte solution is a solution of the enzyme creatinine deiminase (CDI). The sensor surface with charged layer 306 is then contacted 308 with an oppositely charged layer to provide a sensor surface with layered membrane 310. After contacting the sensor surface with charged layer with an oppositely charged polyelectrolyte solution, the sensor surface may be optionally washed. The coating process may be repeated to produce any number of alternating layers within the membrane. The layers may be alternating in charge, but may also comprise one or more neutrally charged layers. The overall charge of the layered membrane may be neutral, for example. The total charge of the layers does not have to be zero. Due to the counter ions floating in the solution into which the layered membrane is immersed, the overall electroneutrality of the layered membrane will include charge distribution from all counter ions. The overall neutrality of the system is maintained by the balance of the charged layers interacting with oppositely charged mobile ions in solution. The layering of multiple charged layers within the membrane produces a high doping, and a relatively thin active immobilized conversion species.

Figure 4:
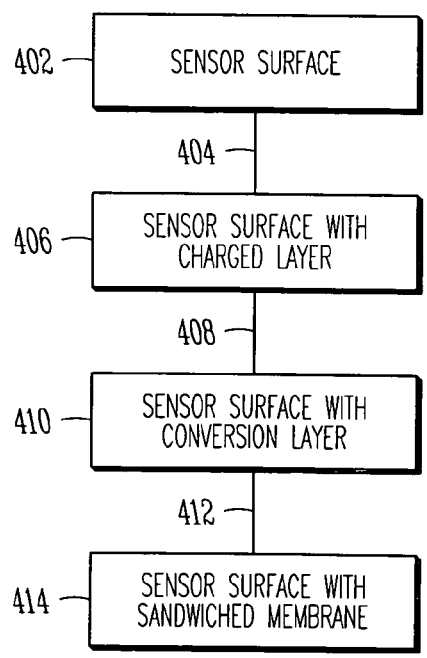
FIG. 4 illustrates a block flow diagram of a method of making a sandwiched membrane on a sensor surface, according to some embodiments of the invention.

Referring to FIG. 4, a block flow diagram of a method 400 of making a sandwiched membrane on a sensor surface is shown, according to some embodiments of the invention. A sensor surface 402 is contacted 404 with a charged layer to create a sensor surface with charged layer 406. The sensor surface with charged layer 406 is then contacted 408 with a conversion layer to provide a sensor surface with conversion layer 410. The conversion species may be an enzyme layer, such as CDI, for example. The sensor surface with conversion layer 410 is contacted 412 with an oppositely charged layer to create a sensor surface with a sandwiched membrane 414. Examples of charged polyelectrolytes are PAH and polystyrene sulfonate (PSS).

Utilizing the methods of FIGS. 3 and 4, the layers within a layered membrane can have a thickness of from about 0.001 micron to about 1000 microns. More specifically, the layers may have a thickness of from about 0.01 micron to about 500 microns. Embodiments of the present invention may provide a layered membrane wherein the outermost layer of the membrane is selected such that its charge is the same as that of the buffering species present in the aqueous fluid. In addition, the outermost layer of the membrane may be positively charged when the aqueous fluid comprises an acidic buffering species, and the outermost layer of the membrane may be negatively charged when the aqueous fluid comprises a basic buffering species The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The invention claimed is:

1. A sensor to detect an analyte in a physiological fluid, comprising:
   a sensor having a surface
   a membrane, in contact with the sensor surface, the membrane comprising:
   an outer layer;
   a plurality of alternating layers of conversion layers comprising an enzyme capable of converting an analyte in a physiological fluid sample into a charged species and polyelectrolyte layers, the polyelectrolyte layers acting as matrices to host the conversion layers, wherein the polyelectrolyte comprises repeating units having an electrolyte group which dissociates in the physiological fluid, making the polyelectrolyte layer negatively charged, wherein the polyelectrolyte layers have a pKa value that differs by two pH units or more than the operating pH of the sensor; and
   wherein the conversion layers and the polyelectrolyte layers are selected to control the exclusion of a negatively charged physiological buffer species found in the physiological fluid sample, thereby enhancing the rate or sensitivity of the conversion of the analyte into a charged species, and wherein the outer layer of the membrane is negatively charged; and
   a transducer adapted to detect the presence or amount of the charged species, thereby detecting the presence or amount of the analyte in a physiological fluid sample.

2. The sensor of claim 1 wherein the selection of the one or mere conversion layers and the polyelectrolyte layers enhances the rate of the conversion of the analyte into a charged species.

3. The sensor of claim 1, wherein the total charge of the combination of conversion layers, the polyelectrolyte layers and mobile ions attracted to the layers in solution is neutral.

4. The sensor of claim 1, wherein the conversion layers and the polyelectrolyte layers comprise a polyelectrolyte.

5. The sensor of claim 1, wherein the polyelectrolyte comprises poly(sodium styrene sulfonate) (PSS), poly(acrylic acid) (PAA), or combinations thereof.

6. The sensor of claim 1, wherein the polyelectrolyte layers have a pKa value lower than about 4.5.

7. A method of detecting a selected analyte in a physiological fluid, the method comprising:
   contacting a physiological fluid sample comprising the analyte and the physiological fluid having a negatively charged buffering species with a layered membrane, sufficient to create an analyte in a buffer selective environment;
   controlling the exclusion of the negatively charged buffering species within the layered membrane thereby enhancing the rate or sensitivity of the conversion of the analyte into a charged species;
   and
   detecting with a sensor the conversion of the analyte, sufficient to provide analyte concentration measurements;
   wherein the layered membrane comprises
   an outer layer;
   a plurality of alternating layers of conversion layers comprising an enzyme capable of converting an analyte into a charged species and polyelectrolyte layers, the polyelectrolyte layers acting as matrices to host the conversion layers, wherein the polyelectrolyte comprises repeating units having an electrolyte group which dissociates in the physiological fluid, making the polyelectrolyte layer negatively charged, wherein the polyelectrolyte layers have a pKa value that differs by two pH units or more than the operating pH of the sensor; and
   wherein the conversion layers and polyelectrolyte layers are selected to control the exclusion of the negatively charged physiological buffer species, and wherein the outer layer of the membrane is negatively charged.

8. The method of claim 7, wherein detecting the conversion of the analyte comprises detection by calorimetric, amperometric, potentiometric, optical, piezo-electric means or combinations thereof.

9. The method of claim 7 wherein the combination of the conversion layers and the polyelectrolyte layers enhances the sensitivity of the conversion.

10. The sensor of claim 1 wherein the physiological buffer species is carbonate ion.

11. The method of claim 7 wherein the buffering species is carbonate ion.

12. The method of claim 7, wherein the polyelectrolyte comprises poly(sodium styrene sulfonate) (PSS), poly(acrylic acid) (PAA), or combinations thereof.

13. The method of claim 7, wherein the polyelectrolyte layers have a pKa value lower than about 4.5.

14. The sensor of claim 1, wherein the analyte is glucose or urea.

15. The method of claim 7, wherein the analyte is glucose or urea.

* * * * *